United States Patent [19]

Gordon et al.

[11] Patent Number: 5,208,042
[45] Date of Patent: May 4, 1993

[54] STABILIZED MERCURIC OXIDE OINTMENT COMPOSITIONS

[75] Inventors: Harry Gordon, Wantagh; Henry Chan, Massapequa; Howard Brasch, Brentwood, all of N.Y.

[73] Assignee: Del Laboratories, Inc., Farmingdale, N.Y.

[21] Appl. No.: 698,287

[22] Filed: May 10, 1991

[51] Int. Cl.$^5$ .................... A01N 59/18; A61K 33/28
[52] U.S. Cl. ................................................. 424/644
[58] Field of Search ......................................... 424/644

[56] References Cited

U.S. PATENT DOCUMENTS 1,493,564  5/1924  Quine ................................... 424/644
2,372,807  4/1945  Brown .................................. 424/644
4,612,193  9/1986  Gordon et al. ....................... 424/644

Primary Examiner—Richard L. Raymond
Assistant Examiner—John D. Pak
Attorney, Agent, or Firm—Kirschstein, Ottinger, Israel & Schiffmiller

[57] ABSTRACT

Oleaginous ointment compositions for topical antibacterial treatment containing about 0.5 to about 1.5% yellow mercuric oxide by weight and additionally containing organic acids selected from the group consisting of alkanoic acids of formula $CH_3(CH_2)_nCOOH$, wherein n is an integer from 4 to 22, and arylalkanoic acids of formula $C_6H_5(CH_2)_nCOOH$, wherein n is an integer from 0 to 17, to increase the color stability of the compositions. A method of making the novel stabilized ointment compositions is also disclosed.

23 Claims, No Drawings

STABILIZED MERCURIC OXIDE OINTMENT COMPOSITIONS

BACKGROUND OF THE INVENTION

1. Field of the Invention

The invention relates to topical antibacterial ointments containing yellow mercuric oxide.

2. Description of the Prior Art

Yellow mercuric oxide, dispersed in an oleaginous ointment base, has been shown to be a safe and effective treatment for topical infections, especially near the eye. However, yellow mercuric oxide is sensitive to light, moisture and reducing agents, producing a green to black discoloration on the outer surface of the exposed yellow mercuric oxide particles. Since the discoloration occurs only at the surface, it is of little more than aesthetic importance and usually does not affect the safety or effectiveness of the yellow mercuric oxide ointment. The discoloration does have a significant effect upon user acceptance, however, and for this reason needs to be prevented.

Many of the prior art ointments containing yellow mercuric oxide also contain a small quantity of boric acid to stabilize the mercuric oxide against color/chemical deterioration. The use of boric acid and related compounds as stabilizers in antibacterial ointments are disclosed, for example, in U.S. Pat. No. 1,493,564. However, even boric acid-containing ointments generally have shelf lives of no more than about six months before serious discoloration of the mercuric oxide active ingredient makes the composition unacceptable to the ordinary consumer/user.

It has been further proposed in the prior art to utilize a combination of boric acid and wheat germ oil to prevent deterioration and discoloration of yellow mercuric oxide in an ointment base, and to potentiate the bactericidal potency of the active ingredient (see U.S. Pat. No. 4,612,193). While ointment compositions containing both boric acid and wheat germ oil have longer shelf life and color stability than other prior art ointment compositions containing mercuric oxide, the problem of discoloration still persists with these compositions. Improved means of stabilizing the yellow mercuric oxide and making it more resistant to discoloration are required.

SUMMARY OF THE INVENTION

It is the object of the present invention to provide ointment compositions for topical antibacterial treatment which contain yellow mercuric oxide and yet have a long shelf life, maintain their bactericidal potency and resist discoloration for long periods of time. In keeping with this object and others which will become apparent hereinafter, the present invention resides, briefly stated, in oleaginous ointment compositions for topical antibacterial treatment containing about 0.5 to about 1.5% yellow mercuric oxide by weight of the composition, the color stability of said composition being improved by the addition thereto of about 0.1 to about 10.0% by weight of a stabilizing compound selected from a specific group of alkanoic acids and arylalkanoic acids, said alkanoic acids having a total chain length of 6 to 24 carbon atoms, and said arylalkanoic acids having a total alkyl chain length of 1 to 18 carbon atoms.

The present invention also comprehends the novel method of stabilizing and retarding discoloration of an ointment composition containing yellow mercuric oxide as its active ingredient by adding to said composition about 0.1 to about 10.0% by weight of a stabilizing compound selected from the group of organic acids defined above.

DETAILED DESCRIPTION OF THE INVENTION

The oleaginous compositions of the present invention may comprise any conventional fatty ointment base, for example a base including white petrolatum and mineral oil, and waxy substances such as microcrystalline wax. The compositions further contain as their topically active bactericidal ingredient from about 0.5 to about 1.5% yellow mercuric oxide by weight of the total composition.

The invention resides in the addition to such ointment compositions containing yellow mercuric oxide of about 0.1 to about 10.0% by weight of a stabilizing compound selected from the group consisting of alkanoic acids of formula $CH_3(CH_2)_nCOOH$, wherein n is an integer from 4 to 22, and arylalkanoic acids of formula $C_6H_5(CH_2)_nCOOH$, wherein n is an integer from 0 to 17. Combinations of more than one of these stabilizing organic acids may be utilized, with the total concentration of the added acids not to exceed about 10.0%.

Preferred alkanoic acids for use as stabilizing compounds in the novel ointment compositions are those in which n is an integer from 14 to 18, i.e., where the total chain length of the acid is from 16 to 20 carbon atoms. Most preferred as an alkanoic stabilizer is stearic acid ($n=16$).

Preferred arylalkanoic acids include those with short alkyl side chains, most preferably benzoic acid.

It has been found, surprisingly, that the addition of 0.1 to 10.0% by weight of one or more of the selected stabilizing compounds described above has a very significant effect in extending the shelf life and color stability of the yellow mercuric oxide ointment compositions. In particular, it has been discovered that when from about 0.15 to about 0.8% by weight of such stabilizing compounds, particularly stearic acid (e.g., in the form of stearic acid, NF), is added to the ointment compositions, the yellow mercuric oxide active ingredient is protected from discoloration for extended periods of time, far longer than can be achieved with either boric acid alone as a stabilizer or the combination of boric acid and wheat germ oil. In fact, yellow mercuric oxide dispersed in an oleaginous ointment base containing one of the selected stabilizing compounds resists light-induced darkening approximately 2 to 10 times longer than the same active ingredient in the identical ointment base without the stabilizing alkanoic or arylalkanoic acids.

By one preferred method, the organic acids used as stabilizing compounds are incorporated into the oleaginous ointment base by mixing with the fatty and waxy base components, melting the base, and subsequently cooling the base to about 40° C. before dispersing the yellow mercuric oxide powder therein. It is believed that by this method, the stabilizing acid concentrates at the interface between the mercuric oxide particles and the surrounding oleaginous ointment, forming a protective barrier around said particles with the polar carboxyl group of the acid oriented toward the polar mercuric oxide surface, and with the hydrocarbon portion of the acid oriented into the surrounding ointment. The said protective barrier requires the polarity of a carboxylic acid group for stable binding since organic alcohols, such as stearyl alcohol, provide no protection against the discoloration of yellow mercuric oxide. It is emphasized, however, that no particular mechanism or theory of action is essential to the practice of the present invention, and the invention is not intended to be limited to any particular physical or chemical mechanism of action for achieving its objectives.

The stabilizing organic acid compounds of the present invention provide not only substantially increased resistance to sunlight-induced darkening of the yellow mercuric oxide in the ointment, but also greatly increase the resistance of the mercuric oxide to darkening by reducing agents in the ointment.

The ointment compositions of the present invention are safe and effective topical antibacterial agents, and are particularly useful for treating styes and other infections of the eyelid. When stabilized in accordance with the method of the present invention, these compositions retain both their efficacy and their high level of user acceptance for extended periods of time.

The following is an illustrative example of a stabilized composition according to the present invention and of the method of making said composition. The example is not intended, however, to set forth specific ingredients, starting materials, conditions or manufacturing procedures which must be practiced exclusively in order to come within the scope of the present invention.

EXAMPLE

An oleaginous ointment composition containing yellow mercuric oxide as its active ingredient was prepared using the following ingredients in the relative weight percentages indicated:

| Ingredients | Percentage Concentration (w/w) |
| --- | --- |
| White Petrolatum, USP | 54.55 |
| Mineral Oil, NF | 31.50 |
| Microcrystalline Wax | 5.00 |
| *Stearic Acid, NF | 0.40 |
| Boric Acid, NF | 2.50 |
| Yellow Mercuric Oxide | 1.05 |
| Wheat Germ Oil | 5.00 |

*Stearic Acid, NF (Triple pressed) Supplier: Emery Industries (Cincinnati, Ohio)

The white petrolatum, mineral oil, microcrystalline wax and stearic acid, NF were charged into a suitably sized #316 stainless steel tank with an agitator. The ointment base was heated while mixing to 80°-85° C. until the base was completely melted. The ointment base was then filtered through a 0.22 micro membrane filtering unit into the main #316 stainless steel mixing tank.

When the ointment base had cooled down to about 45° C., a portion of the base was withdrawn into a stainless steel container. The boric acid (sterilized) was then added to the base and dispersed with the aid of a homomixer for 10 minutes. The yellow mercuric oxide (sterilized) was then added to the mixture and dispersed for at least 30 minutes until a homogeneous slurry was achieved.

The slurry was added to the main ointment batch and mixed until the batch was homogeneous and free of lumps. The batch was then cooled to about 28° C. and the filtered wheat germ oil added thereto. The resulting ointment was mixed for about 15 minutes until homogeneous.

It has thus been shown that there are provided compositions and methods which achieve the various objects of the invention and which are well adapted to meet the conditions of practical use.

As various possible embodiments might be made of the above invention, and as various changes might be made in the embodiments set forth above, it is to be understood that all matters herein described are to be interpreted as illustrative and not in a limiting sense.

What is claimed as new and desired to be protected by Letters Patent is set forth in the following claims:

1. An oleaginous ointment composition for topical antibacterial treatment containing about 0.5 to about 1.5% yellow mercuric oxide by weight of the composition, wherein the improvement comprises increasing the color stability of the composition by the addition thereto of about 0.1 to about 10.0% by weight of a stabilizing compound selected from the group consisting of alkanoic acids of formula $CH_3(CH_2)_nCOOH$, wherein n is an integer from 4 to 22, benzoic acid and arylalkanoic acids of formula $C_6H_5(CH_2)_nCOOH$, wherein n is an integer from 1 to 17.

2. A composition according to claim 1 wherein said stabilizing compound is an alkanoic acid and n is an integer from 14 to 18.

3. A composition according to claim 2 wherein said stabilizing compound is stearic acid.

4. A composition according to claim 3 wherein said stearic acid is in the form of stearic acid, NF.

5. A composition according to claim 1 wherein said stabilizing compound is an arylalkanoic acid.

6. A composition according to claim 1 wherein said stabilizing compound is benzoic acid.

7. A composition according to claim 1 which comprises from about 0.15 to about 0.8% by weight of said stabilizing compound.

8. A composition according to claim 7 which comprises about 0.4% by weight stearic acid, NF.

9. A composition according to claim 1 which additionally comprises from about 2 to about 10% wheat germ oil and from about 2 to about 10% boric acid by weight of the composition.

10. A composition according to claim 1 which comprises an ointment base including white petrolatum and mineral oil.

11. A composition according to claim 10 wherein said ointment base additionally comprises microcrystalline wax.

12. A composition according to claim 1 wherein said topical antibacterial treatment is the treatment of styes or related infections of the eyelid.

13. A method of stabilizing and retarding discoloration of an ointment composition having an oleaginous base and containing about 0.5 to about 1.5% yellow mercuric oxide by weight of the composition, comprising the addition to the composition of about 0.1 to about 10.0% by weight of a stabilizing compound selected from the group consisting of alkanoic acids of formula $CH_3(CH_2)_nCOOH$, wherein n is an integer from 4 to 22 benzoic acid and arylalkanoic acids of formula $C_6H_5(CH_2)_nCOOH$, wherein n is an integer from 1 to 17.

14. A method according to claim 13 wherein said stabilizing compound is an alkanoic acid and n is an integer from 14 to 18.

15. A method according to claim 14 wherein said stabilizing compound is stearic acid.

16. A method according to claim 15 wherein said stearic acid is in the form of stearic acid, NF.

17. A method according to claim 13 wherein said stabilizing compound is an arylalkanoic acid.

18. A method according to claim 13 wherein said stabilizing compound is benzoic acid.

19. A method according to claim 13 wherein said stabilizing compound constitutes from about 0.15 to about 0.8% by weight of said composition.

20. A method according to claim 19 wherein said composition is stabilized with about 0.4% stearic acid, NF.

21. A method according to claim 13 wherein said composition additionally comprises from about 2 to about 10% wheat germ oil and from about 2 to about 10% boric acid by weight of the composition.

22. A method according to claim 13 wherein said stabilizing compound is added to the ointment base prior to the addition thereto of the yellow mercuric oxide, after which the ointment base is melted and subsequently cooled to about 40° C., whereupon the yellow mercuric oxide is dispersed within the ointment base.

23. A method according to claim 22 wherein said ointment base is melted at a temperature of about 80°-85° C.

* * * * *